(12) United States Patent
Gibson et al.

(10) Patent No.: US 7,358,209 B2
(45) Date of Patent: Apr. 15, 2008

(54) POLYMERISATION CATALYSTS

(75) Inventors: Vernon Charles Gibson, London (GB); Grant Berent Jacobsen, Tervuren (BE); David John Jones, London (GB); Richard James Long, Leeds (GB)

(73) Assignee: Ineos Europe Limited, Hampshire (GB)

( * ) Notice: Subject to any disclaimer, the term of this patent is extended or adjusted under 35 U.S.C. 154(b) by 0 days.

(21) Appl. No.: 11/513,205

(22) Filed: Aug. 31, 2006

(65) Prior Publication Data
US 2006/0293473 A1 Dec. 28, 2006

Related U.S. Application Data

(62) Division of application No. 10/548,275, filed as application No. PCT/GB2004/000141 on Mar. 18, 2004, now Pat. No. 7,144,839.

(30) Foreign Application Priority Data

Mar. 19, 2003 (GB) ................................. 0306308.8

(51) Int. Cl.
C08F 4/68 (2006.01)
C08F 4/622 (2006.01)
C08F 4/623 (2006.01)
C08F 210/00 (2006.01)

(52) U.S. Cl. .................. 502/209; 502/103; 502/162; 502/171; 526/161; 526/172; 526/169; 556/21; 556/42

(58) Field of Classification Search ............... 502/162, 502/103, 171, 209; 526/161, 172, 169; 55/13, 55/42; 556/21, 42
See application file for complete search history.

(56) References Cited

U.S. PATENT DOCUMENTS 6,559,326 B1 * 5/2003 Kristen et al. ................ 556/21
2002/0193536 A1 12/2002 Kashiwamura et al.

OTHER PUBLICATIONS

Klein, H.F., et al; "Synthesis and Reactions with CO and $C_2H_4$ of Cobalt (I) Complexes Containing Trimethylphosphine and Chelting o-Diphenylphosphanyl-phenolate Ligands"; *Chemical Sciences*; vol. 53, No. 3; pp. 307-314; (1998).

Heinicke, J., et al; "Methyl(2-phosphanylphenolato[P,0])nickel(II) Complexes—Synthesis, Structure, and Activity as Ethene Oligomerization Catalysts"; *Eur. J. Inorg. Chem.*; pp. 431-440 (2000).

Braunstein, P., et al; "A quasi-covalent metal-metal bond in an early-1te heterobimetallic Ti-Pt complex stabilized by phosphinoenolate ligands"; *Chemical Communications*; pp. 610-611 (2003).

Willoughby, C.A., et al; "Preparation of Novel Titanium Complexes Bearing o-Phospinophenol Ligands"; *Organometallics*; vol. 15; pp. 472-475 (1996).

Heinicke, J., et al.; "Nickel Chelate Complexes of 2-Alkylphenylphosphanylphenolates: Synthesis, Structural Investigation and Use in Ethylene Polymerization"; *Eur. J. Inorg. Chem.*; pp. 299-305 (2000).

Knowles, W.S., et al; "Studies of Asymmetric Homogeneous Catalysts"; *STN Chemical Abstracts*; vol. 9, No. 97; pp. 325-336 (1982).

* cited by examiner

*Primary Examiner*—Caixia Lu
(74) *Attorney, Agent, or Firm*—Nixon & Vanderhye

(57) ABSTRACT

A transition metal complex having the following Formula (A): wherein the monovalent groups $R^1$ and $R^2$ are —$R^a$, —$OR^b$, —$NR^cR^d$, and —$NHR^e$: the monovalent groups $R^a$, $R^b$, $R^c$, $R^d$ and $R^e$, and the divalent group $R^3$ are (i) aliphatic hydrocarbon, (ii) alicyclic hydrocarbon, (iii) aromatic hydrocarbon, (iv) alkyl substituted aromatic hydrocarbon (v) heterocyclic groups and (vi) heterosubstituted derivatives of said groups (i) to (v); M is a Group (3) to (11) or lanthanide metal; E is phosphorus or arsenic; X is an anionic group, L is a neutral donor group; n is (1) or (2), y and z are independently zero or integers, such that the number of X and L groups satisfy the valency and oxidation state of the metal M. n is preferably (2) and the two resulting $R^1$ groups are preferably linked. The complex can be used with optional activator to polymerise olefins (A)

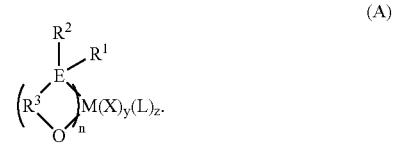

20 Claims, No Drawings

POLYMERISATION CATALYSTS

This application is a divisional of application Ser. No. 10/548,275, filed Sep. 7, 2005 now U.S. Pat. No. 7,144,839, which is a 371 of PCT/GB04/001141, filed 18 Mar. 2004, which claims priority to British Application No. 0306308.8, filed 19 Mar. 2003, the entire content of which is hereby incorporated by reference in this application.

The present invention relates to transition metal-based polymerisation catalysts and to their use in the polymerisation and copolymerisation of olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last three decades, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent, or, in the case of propylene, in bulk.

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so-called "low density" polyethylene produced by the high pressure free radical catalysed polymerisation of ethylene. Such polymers and copolymers are used extensively in the manufacture of flexible blown film.

Polypropylenes are also commercially produced in a variety of different types and grades. Homopolymerisation of propylene with transition metal based catalysts leads to the production of grades with a wide variety of applications. Copolymers of propylene with ethylene or terpolymers with ethylene and higher 1-olefins are also useful materials.

In recent years the use of certain metallocene catalysts (for example biscyclopentadienylzirconiumdichloride activated with alumoxane) has provided catalysts with potentially high activity. Other derivatives of metallocenes have been shown to be potentially useful for producing polypropylene with good activity, molecular weight and tacticity control. However, metallocene catalysts of this type suffer from a number of disadvantages, for example, high sensitivity to impurities when used with commercially available monomers, diluents and process gas streams, the need to use large quantities of expensive alumoxanes to achieve high activity, difficulties in putting the catalyst on to a suitable support and synthetic difficulties in the production of more complex catalyst structures suitable for polymerising propylene in a tactic manner.

An object of the present invention is to provide a novel transition metal complex which can be used, optionally with an activator, for polymerising unsaturated monomers. A further object of the present invention is to provide catalyst system and a process for polymerising monomers, for example, olefins, and especially for polymerising ethylene alone or propylene alone, or for copolymerising ethylene with higher 1-olefins with high activity.

One aspect of the present invention provides a novel transition metal complex having the following Formula A:

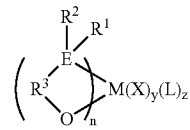

Formula A wherein the monovalent groups $R^1$ and $R^2$ are independently selected from $-R^a$, $-OR^b$, $-NR^cR^d$, and $-NHR^e$:

the monovalent groups $R^a$, $R^b$, $R^c$, $R^d$, and $R^e$, and the divalent group $R^3$ are independently selected from (i) aliphatic hydrocarbon, (ii) alicyclic hydrocarbon, (iii) aromatic hydrocarbon, (iv) alkyl substituted aromatic hydrocarbon (v) heterocyclic groups and (vi) heterosubstituted derivatives of said groups (i) to (v); M is a metal from Group 3 to 11 of the Periodic Table or a lanthanide metal; E is phosphorus or arsenic; X is an anionic group, L is a neutral donor group; n is 1 or 2, y and z are independently zero or integers such that the number of X and L groups satisfy the valency and oxidation state of the metal M.

The monovalent groups $R^a$, $R^b$, $R^c$, $R^d$, and $R^e$, and the divalent group $R^3$ are defined above as (i) aliphatic hydrocarbon, (ii) alicyclic hydrocarbon, (iii) aromatic hydrocarbon, (iv) alkyl substituted aromatic hydrocarbon (v) heterocyclic groups, (vi) heterosubstituted derivatives of said groups (i) to (v). These defined groups preferably contain 1 to 30, more preferably 2 to 20, most preferably 2 to 12 carbon atoms. Examples of suitable monovalent aliphatic hydrocarbon groups are methyl, ethyl, ethenyl, butyl, hexyl, isopropyl and tert-butyl. Examples of suitable monovalent alicyclic hydrocarbon groups are adamantyl, norbornyl, cyclopentyl and cyclohexyl. Examples of suitable monovalent aromatic hydrocarbon groups are phenyl, biphenyl, naphthyl, phenanthrenyl and anthacenyl. Examples of suitable monovalent alkyl substituted aromatic hydrocarbon groups are benzyl, tolyl, mesityl, 2,6-diisopropylphenyl and 2,4,6-triisopropyl. Examples of suitable monovalent heterocyclic groups are 2-pyridinyl, 3-pyridinyl, 2-thiophenyl, 2-furanyl, 2-pyrrolyl, 2-quinolinyl. As regards the divalent group $R^3$, this, for example, can be selected from any of the aforementioned monovalent groups wherein one of the hydrogen atoms on the said monovalent group is replaced by a valency bond to form the second bond on the divalent group $R^3$.

Suitable substituents for forming heterosubstituted derivatives of said groups $R^a$, $R^b$, $R^c$, $R^d$, $R^e$ and $R^3$ are, for example, chloro, bromo, fluoro, iodo, nitro, amino, cyano, alkoxy, mercapto, hydroxyl and silyl. Examples of alkoxy groups are methoxy, ethoxy, phenoxy (i.e. $-OC_6H_5$), tolyloxy (i.e. $-C_6H_4(CH_3)$), xylyloxy, mesityloxy. Examples of amino groups are dimethylamino, diethylamino, methylethylamino. Examples of mercapto groups are thiomethyl, thiophenyl. Examples of silyl groups are trimethylsilyl and triethylsilyl. Examples of suitable heterosubstituted derivatives of said groups (i) to (v) are 2-chloroethyl, 2-bromocyclohexyl, 2-nitrophenyl, 4-ethoxyphenyl, 4-chloro-2-pyridinyl, 4-dimethylaminophenyl and 4-methylaminophenyl.

$R^1$ and $R^2$ can, if desired, form a single integral divalent group $R^4$, wherein $R^4$ is independently selected from the divalent groups —$R^{a'}$—, —O—$R^{b'}$—, —$R^{b'}$—O—, —N—($R^c$)$R^{d'}$—, —N($R^c$)—, —N($R^c$)—$R^{d'}$—N($R^c$)—, —Si($R^c$)$_2$—$R^{a'}$—Si($R^c$)$_2$—, and —Si($R^c$)$_2$—; and wherein the divalent groups $R^{a'}$, $R^{b'}$, and $R^{d'}$ are independently selected from divalent (i) aliphatic hydrocarbon, (ii) alicyclic hydrocarbon, (iii) aromatic hydrocarbon, (iv) alkyl substituted aromatic hydrocarbon (v) heterocyclic groups and (vi) heterosubstituted derivatives of said groups (i) to (v), and $R^c$ is as defined above.

Although $R^1$ and $R^2$ can form integral unit $R^4$ it is preferred that they are separate groups. Preferably $R^1$ and $R^2$ are separate, identical groups. Preferably, $R^1$ and $R^2$ are separate, identical aliphatic hydrocarbon, alicyclic hydrocarbon, aromatic hydrocarbon or alkyl substituted aromatic hydrocarbon groups.

When n=2, there are two phosphorus or arsenic-containing ligands on the transition metal M. Under these circumstances there are two separate $R^1$ groups ($R^{1'}$ and $R^{1''}$) and two separate $R^2$ groups ($R^{2'}$ and $R^{2''}$). It is preferred that at least one of the pairs of these groups, $R^{1'}$ and $R^{1''}$ or $R^{2'}$ and $R^{2''}$ are linked. For example, $R^{1'}$ and $R^{1''}$ can be linked to form $R^5$ as illustrated in Formula B below.

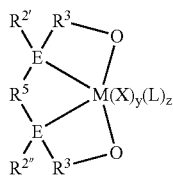

Formula B

The divalent group $R^5$ is preferably selected from the divalent groups recited above for the divalent group $R^4$.

Thus the present invention further provides a transition metal complex wherein n=2 and the $R^1$ groups on the two units

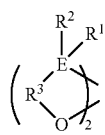

are linked to form $R^5$ such that Formula A becomes Formula B below.

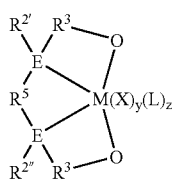

Formula B wherein the divalent group $R^5$ is selected from the divalent groups —$R^{a'}$—, —O—$R^{b'}$—, —O—$R^{b'}$—O—, —N—($R^c$)$R^{d'}$—, —N($R^c$)—, —N($R^c$)—$R^{d'}$—N($R^c$)—, —Si($R^c$)$_2$—$R^{a'}$—Si($R^c$)$_2$—, and —Si($R^c$)$_2$—; the divalent groups $R^{a'}$, $R^{b'}$, and $R^{d'}$ being independently selected from divalent (i) aliphatic hydrocarbon, (ii) alicyclic hydrocarbon, (iii) aromatic hydrocarbon, (iv) alkyl substituted aromatic hydrocarbon (v) heterocyclic groups and (vi) heterosubstituted derivatives of said groups (i) to (v).

M is preferably a Group 3 to 11 transition metal, more preferably Group 5 to 7 transition metal. Most preferably M is vanadium. M can also be a Group 3 to 6 transition metal.

Examples of groups suitably used as the divalent group $R^5$ are —$CH_2$—, —$CH_2CH_2$—, —$CH_2CH_2CH_2$—, trans-1,2-cyclopentane, trans-1,2-cyclohexane, 2,3-butane, 1,1'-biphenyl, 1,1'-binaphthyl, —N(Me)-, —N(Et)-, 1,1'-biphenol and —Si(Me)$_2$-.

The divalent group $R^3$ is defined above as independently selected from (i) aliphatic hydrocarbon, (ii) alicyclic hydrocarbon, (iii) aromatic hydrocarbon, (iv) alkyl substituted aromatic hydrocarbon (v) heterocyclic groups and (vi) heterosubstituted derivatives of said groups (i) to (v). It is preferred that $R^3$ is an alkyl substituted or heterosubstituted aromatic hydrocarbon group. More preferably $R^3$ is an alkyl substituted or heterosubstituted divalent 1,2-phenylene group. The 1,2-phenylene group preferably has the said alkyl substitutuent or hetero atom in the position ortho to the ring-carbon atom bonded to the oxygen atom in Formula A. The 1,2-phenylene group is optionally substituted in one of more of the other remaining positions of the 1,2-phenylene group.

When any of the defined monovalent groups $R^a$, $R^b$, $R^c$, $R^d$, and $R^e$, and the divalent groups $R^{a'}$, $R^{b'}$, $R^{d'}$, $R^3$, $R^4$, and $R^5$ are heterocyclic, the atom or atoms present in the rings as the heteroatom can be, for example, oxygen, nitrogen, sulphur, phosphorus or silicon.

E is preferably phosphorus.

M is a metal selected from Groups 3 to 11 of the Periodic table, more preferably selected from Groups 3 to 7. It can also be selected from Groups 3 to 6. M is preferably vanadium.

The anionic group X can be, for example, a halide, preferably chloride or bromide; or a hydrocarbyl group, for example, methyl, benzyl or phenyl; a carboxylate, for example, acetate or acetylacetate; an oxide; an amide, for example diethyl amide; an alkoxide, for example, methoxide, ethoxide or phenoxide; an acetylacetonate; or a hydroxyl. Or, for example, X can be a non-coordinating or weakly-coordinating anion, for example, tetrafluoroborate, a fluorinated aryl borate or a triflate. The anionic groups X may be the same or different and may independently be monoanionic, dianionic or trianionic.

The neutral donor group L can be, for example, a solvate molecule, for example diethyl ether or THF (tetrahydrofuran); an amine, for example, diethyl amine, trimethylamine or pyridine; a phosphine, for example trimethyl phosphine or triphenyl phosphine; an olefin; water; a conjugated or non-conjugated diene.

The value of y in Formula A and B depends on the value of n, the charge on the anionic group X and the oxidation state of the metal M. For example, if M is titanium in oxidation state+4 and n is 2, then y is 2 if X is a monoanionic group (eg. chloride) or y is 1 if X is a dianionic group (eg. oxide); if M is titanium in oxidation state+4 and n is 1, then y is 3 if all X groups are monoanionic groups (eg. chloride) or y is 2 if one X group is a dianionic group (eg. oxide) and the other is monoanionic. It is preferred that n is 2.

Particularly preferred complex compounds are those having the formulae

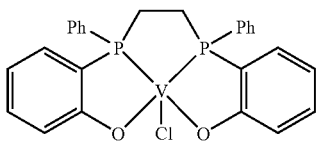

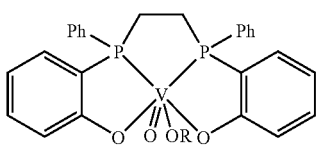

In the present invention the complex compounds having the Formula A and Formula B can be catalytically active by themselves, or may require the use of an activator to render them sufficiently active for use in commercial polymerisation processes. Accordingly, the present invention further comprises a catalyst system for the polymerisation of unsaturated monomer comprising (1) a complex compound having the Formula A or Formula B as hereinbefore defined and optionally (2) an activator compound.

The activator compound employed in the catalyst system of the present invention is suitably selected from organoaluminium compounds and organoboron compounds. Suitable organoaluminium compounds include trialky- or triarylaluminium compounds, for example, trimethylaluminium, triethylaluminium, tributylaluminium, tri-n-octylaluminium, ethylaluminium dichloride; diethylaluminium chloride, methylaluminium dichloride, dimethylaluminium chloride, tris(pentafluorophenyl)aluminium and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear, cyclic and cage compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable organoboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl) boron. Mixtures of organoaluminium compounds and organoboron compounds may be used.

In the preparation of the catalysts of the present invention the quantity of activating compound selected from organoaluminium compounds and organoboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of M present in the compound of Formula A or B.

EP1238989 discloses the use of activators (Lewis acids) selected from (b-1) ionic-bonding compounds having a $CdCl_2$ type or a $CdI_2$ type of layered crystal structure;

(b-2) clays, clay minerals, or ion-exchange layered compounds;

(b-3) heteropoly-compounds; and (b-4) halogenated lanthanoid compounds.

The activator employed in the activated catalyst of the present invention may be of the type disclosed in EP1238989 if desired. Such Lewis acids are those compounds which capable of receiving at least one electron pair and is capable of forming an ion pair by reaction with the transition metal complex. The Lewis acid includes the afore-mentioned (b-1) ionic-bonding compounds having a layered crystal structure of a $CdCl_2$ type or $CdI_2$ type (b-2) clay, clay minerals, or ion-exchange layered compounds, (b-3) heteropoly compounds, and (b-4) halogenated lanthanoid compounds. The Lewis acid further includes $SiO_2$, $Al_2O_3$, natural and synthetic zeolites which have Lewis acid points formed by heating or a like treatment, and complexes and mixtures thereof.

U.S. Pat. No. 6,399,535 discloses a coordinating catalyst system capable of polymerizing olefins comprising:

(I) as a pre-catalyst, at least one non-metallocene, non-constrained geometry, bidentate ligand containing transition metal compound or tridentate ligand containing transition metal compound capable of (A) being activated upon contact with the catalyst support-activator agglomerate of (II) or (B) being converted, upon contact with an organometallic compound, to an intermediate capable of being activated upon contact with the catalyst support-activator agglomerate of (II), wherein the transition metal is at least one member selected from Groups 3 to 10 of the Periodic table; in intimate contact with (II) catalyst support-activator agglomerate comprising a composite of (A) at least one inorganic oxide component selected from $SiO_2$, $Al_2O_3$, MgO, $AlPO_4$, $TiO_2$, $ZrO_2$, and $Cr_2O_3$ and (B) at least one ion containing layered material having interspaces between the layers and sufficient Lewis acidity, when present within the catalyst support-activator agglomerate, to activate the pre-catalyst when the pre-catalyst is in contact with the catalyst support-activator agglomerate, said layered material having a cationic component and an anionic component, wherein said cationic component is present within the interspaces of the layered material, said layered material being intimately associated with said inorganic oxide component within the agglomerate in an amount sufficient to improve the activity of the coordinating catalyst system for polymerizing ethylene monomer, expressed as Kg. of polyethylene per gram of catalyst system per hour, relative to the activity of a corresponding catalyst system employing the same pre-catalyst but in the absence of either Component A or B of the catalyst support-activator agglomerate; wherein the amounts of the pre-catalyst and catalyst support-activator agglomerate which are in intimate contact are sufficient to provide a ratio of micromoles of pre-catalyst to grams of catalyst support-activator agglomerate of from about 5:1 to about 500:1. The layered material can be, for example, a smectite clay. The catalyst system of the present invention can be employed with a catalyst support-activator agglomerate as described in U.S. Pat. No. 6,399,535 if desired.

In addition to the activator compound, it can be advantageous to employ catalytic quantities of certain halogenated compounds that are capable of promoting catalyst activity. Promotors of this type are especially useful in the case that the transition metal in the complex is vanadium. U.S. Pat. No. 5,191,042 discloses that certain vanadium-based catalysts activated with organoaluminium compounds can be promoted using a variety of halogenated organic compounds, for example, carbon tetrachloride, hexachloroethylene, benzylbromide, benzylchloride and 2,3- or 1,3-dichloropropylene. Other examples of halogenated organic compounds that can be used in this manner are ethyl trichloroacetate, chloroform ($CHCl_3$) and n-butylchloride. U.S. Pat. No. 5,191,042 also refers to the disclosure of Cooper (T. A Cooper, Journ. Am. Chem. Soc., 4158 (1973), which defines in Table 1 an organic halide activity index based on the ability of the halide to oxidize certain vanadium compounds under standard conditions. For example, carbon tetrachloride is assigned a reactivity of 1 in tetrahydrofuran at 20° C., and other listed halogenated organic compounds have reactivities of from about 0.02 to greater than 200 relative to carbon tetrachloride. When it is desired to use a halogenated promotor, it is preferred to use those having a Cooper Index ranging from about 0.01 up to about 30. The use of such promoters, especially in combination with vanadium-based catalysts is generally well known in the art, and for details of use of the such promoters reference may be made to U.S. Pat. No. 5,191,042 and to other prior art in this field. In the present invention it is possible to employ any halogenated organic compound as a promoter, but the compounds mentioned above are preferred.

The catalyst of the present invention can, if desired, be utilised on a support material. Suitable support materials are, for example, silica, alumina, or zirconia, magnesia, magnesium chloride or a polymer or prepolymer, for example polyethylene, polystyrene, or poly(aminostyrene).

The following are examples of transition metal complexes that can be employed as the catalyst of the present invention, or as the transition metal component of the catalysts system of the present invention:

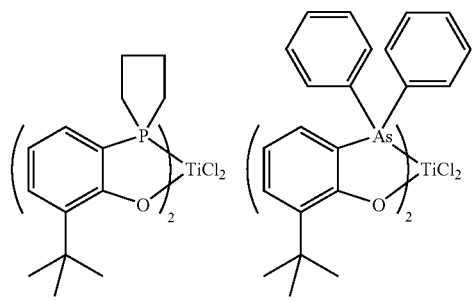

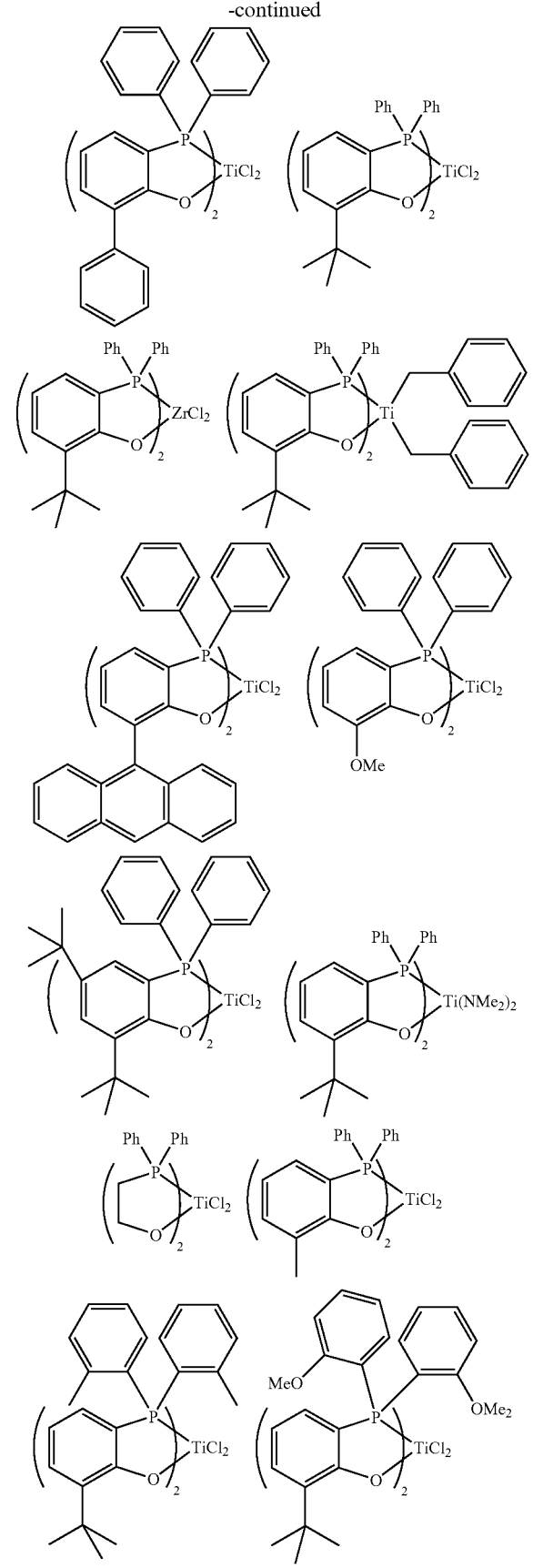

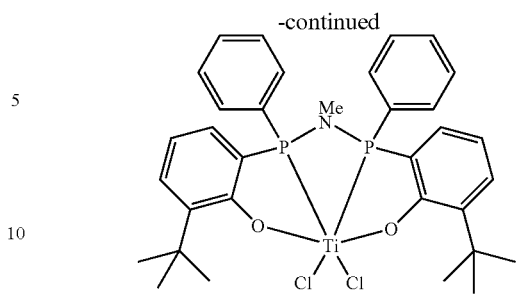
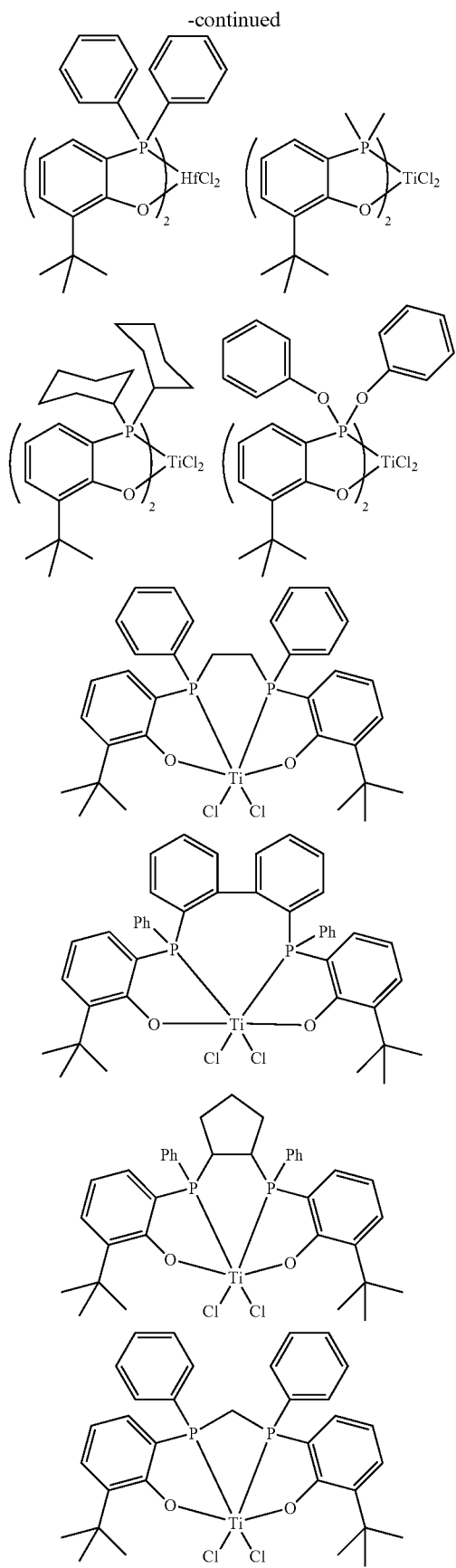

The catalyst or catalyst system of the present invention can if desired comprise more than one of the defined transition metal compounds.

In addition to said one or more defined transition metal compounds, the catalyst or catalyst system of the present invention can also include one or more other types of transition metal compounds or catalysts, for example, transition metal compounds of the type used in conventional Ziegler-Natta catalyst systems, metallocene-based catalysts, or heat activated supported chromium oxide catalysts (e.g. Phillips-type catalyst). The catalyst or catalyst system of the present invention can also used in conjunction with other catalysts producing only 1-olefins, either inside or outside the polymerisation reactor, and in this way make copolymers of ethylene or propylene and these 1-olefins. Suitable catalysts for producing 1-olefins may produce only 1-butene, only 1-hexene or a distribution (for example, a Schulz-Flory distribution) of 1-olefins.

If desired, the catalyst or catalyst system can be formed in situ in the presence of the support material, or the support material can be pre-impregnated or premixed, simultaneously or sequentially, with one or more of the catalyst components. The catalyst and catalyst system of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins, cycloolefins or dienes comprising contacting the monomeric olefin under polymerisation conditions with the polymerisation catalyst of the present invention.

Suitable monomers for use in making homopolymers using the polymerisation process of the of the present invention are, for example, ethylene, propylene, butene, hexene, and styrene. Preferred monomers are ethylene and propylene.

Suitable monomers for use in making copolymers using the polymerisation process of the present invention are ethylene, propylene, 1-butene, 1-hexene, 4 methylpentene-1, 1-octene, methyl methacrylate, methyl acrylate, butyl acrylate, acrylonitrile, vinyl acetate, vinyl chloride, styrene and dienes, such as butadiene or hexadiene and cycloolefins, such as norbornene.

A particularly preferred process in accordance with the present invention is the copolymerisation of ethylene and or propylene with comonomers selected from 1-olefins, acrylic acid esters, vinyl esters and vinyl aromatic compounds. Examples of suitable comonomers are 1-butene, 1-hexene, 4-methylpentene-1, methyl methacrylate, methyl acrylate, butyl acrylate, acrylonitrile, vinyl acetate, and styrene.

Preferred polymerisation processes are the homopolymerisation of ethylene or the homopolymerisation of propylene or copolymerisation of ethylene with one or more of propylene, butene, hexane-1 and 4-methylpentene-1.

Also preferred is a process for the copolymerisation of ethylene and or propylene with comonomers selected from 1-butene, 1-hexene, 4-methylpentene-1, methyl methacrylate, methyl acrylate, butyl acrylate, acrylonitrile, vinyl acetate, and styrene, diene, cyclic olefin, norbornene and substituted norbornene.

The polymerisation conditions can be, for example, bulk phase, solution phase, slurry phase or gas phase. If desired, the catalyst can be used to polymerise ethylene under high pressure/high temperature process conditions wherein the polymeric material forms as a melt in supercritical ethylene. Preferably the polymerisation is conducted under gas phase fluidised or stirred bed conditions.

Slurry phase polymerisation conditions or gas phase polymerisation conditions are particularly useful for the production of high-density grades of polyethylene. In these processes the polymerisation conditions can be batch, continuous or semi-continuous. In the slurry phase process and the gas phase process, the catalyst is generally fed to the polymerisation zone in the form of a particulate solid. This solid can be, for example, an undiluted solid catalyst system formed from the complex of Formula A or B and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymerisation is supported on a support material. Most preferably the catalyst system is supported on a support material prior to its introduction into the polymerisation zone. Suitable support materials are, for example, magnesium chloride, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, eg of the type well know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the polymerisation process of the present invention the process conditions are preferably gas phase fluidised or stirred bed polymerisation conditions.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

The present invention further provides novel compound having the Formula C, suitable for forming a transition metal complex

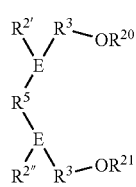

Formula C wherein $R^3$, $R^2$, $R^5$ and E are as defined above and $R^{20}$ and $R^{21}$ are monovalent groups as defined for $R^2$ or hydrogen.

Preferably the ligand has the formula:

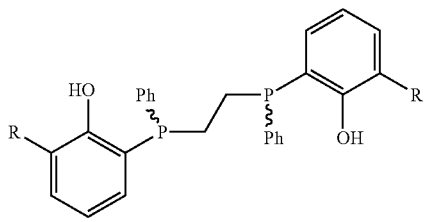

In a further embodiment of the present invention there is provided a process for the preparation of a catalytically active species comprising reacting together (a) a ligand having the Formula C

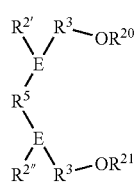

Formula C (b) a transition metal compound $M(L)_n$ and optionally
(c) an activator wherein $R^3$, $R^2$, $R^5$ and E are as defined above and $R^{20}$ and $R^{21}$ are monovalent groups as defined for $R^2$ or hydrogen, the transition metal M is selected from Groups 3 to 11, preferably vanadium, L is independently selected from halide (for example F, Cl, Br, I), alkyl, substituted allyl, cycloalkyl, substituted cycloalkyl; heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, ethers, thioethers and combinations thereof; and neutral donor group, for example, ethers, amines, thioethers, phosphines and the like, optionally two or more L groups may be linked together in a ring structure and n is 1, 2, 3, 4, 5, or 6.

The activator can be any of the activators described throughout this specification. The reaction is preferably conducted in a hydrocarbon solvent. The catalytic species can be used to polymerise monomers in the manner described above for the catalyst of the present invention.

The invention is further illustrated with reference to the following Examples. In the Examples all manipulations of air/moisture-sensitive materials were performed on a conventional vacuum/inert atmosphere (nitrogen) line using standard Schlenk line techniques, or in an inert atmosphere glove box.

EXAMPLE 1

Catalyst Synthesis

EXAMPLE 1a

Synthesis of 1-tert. butyl-2-(methoxymethoxy)benzene

The following reaction was carried out in an efficient fume cupboard. To a rapidly stirred and cooled (0° C.) suspension of Na (5.52 g, 240 mmol) in dry THF (80 ml) under a nitrogen atmosphere was slowly added 2-tert-butylphenol (38.8 ml, 200 mmol). The suspension was stirred at room temperature for 3 h and the green solution filtered into a two-neck flask fitted with a reflux condenser. Separately, acetyl chloride (21.98 g, 280 mmol) was added very slowly to dimethoxymethane (22.83 g, 300 mmol) containing $ZaCl_2$ (50 mg) at 0° C. under a nitrogen atmosphere. The mixture was then stirred at room temperature for 1.5 h to give methoxychloromethane, which was added portion-wise to the solution of deprotonated alcohol. The mixture was stirred at room temperature for 1 h during which a white precipitate formed. The reaction was then quenched with water (100 ml) and diluted with EtOAc (50 ml). The organic layer was separated and washed with 1M NaOH (2×75 ml), 3M NaCl (1×100 ml), dried ($MgSO_4$), filtered, and the solvent removed under vacuum overnight giving crude 1-tertbutyl-2-(methoxymethoxy)benzene as a yellow liquid. The product was further purified by column chromatography [alumina (neutral, +3% $H_2O$); hexane] (33.41 g, 172 mmol, 86% yield). $^1H$ NMR ($CDCl_3$): δ 7.35-6.65 (m, 4H, Ar-L), 5.27 (s, 2H, $OCH_2O$), 3.54 (s, 3H, $OCH_3$), 1.43 (s, 9H, $C(CH_3)_3$).

EXAMPLE 1b

Synthesis of 2-tertbutyl-6-(diphenylphosphino)phenol—("Compound 1")

To a slurry of 1-tert-butyl-2-(methoxymethoxy)benzene (9.714 g, 50 mmol) in ether (50 ml) was added n-butyl-lithium (2.5M in hexanes, 20 ml, 50 mmol) and the mixture stirred for 12 h. Chlorodiphenylphosphine (10.8 ml, 60 mmol) was added to the solution dropwise at −78° C. The mixture was then stirred at room temperature for 2 h.

Degassed 2M HCl (50 ml) was added followed by degassed water (150 ml) and ether (100 ml). The layers were separated and the solvent removed from the organic fraction. The crude yellow oil was dissolved in THF (50 ml) and 5M HCl (5 ml) added. The mixture was stirred and heated at 50° C. for 3 h. After cooling, ether (30 ml) and water (100 ml) added giving a white precipitate of HCl. This precipitate was collected by filtration, slurried with THF (75 ml) and aqueous ammonia (100 ml) slowly added. The layers were separated and the organic fraction further washed with aqueous ammonia (3×50 ml), brine (75 ml) and dried over $Na_2SO_4$. The solution was filtered and the solvent removed to give a thick oil. This was further purified by column chromatography [alumina (neutral, +3% $H_2O$); hexane] to give ("Compound 1") as a thick oil (10.533 g, 32 mmol, 63% yield). Micro Anal. Calcd for $C_{22}H_{23}OP$: C, 79.02; H, 6.93. Found: C, 78.90; H, 6.81. $^1H$ NMR ($C_6D_6$): δ 7.32-7.22 (several m, 5H, Ar—H, 7.02-6.95 (several m, 7H, Ar—H) 6.72 (t, 1H, $^3J(HH)$=7.6 Hz, Ar—H) 1.50 (s, 9H, $C(CH_3)_3$). $^{13}C\{^1H\}$ NMR ($C_6D_6$): δ 158.9 (d, $^2J(PC)$=20 Hz, Ar—C,), 136.5, 135.6, 133.7, 133.5, 133.0, 129.6, 129.1, 129.0, 128.8, 121.5, 120.1 (Ar—C), 35.2 ($C(CH_3)_3$), 29.8 ($C(CH_3)_3$). $^{31}P\{^1H\}$ NMR ($C_6D_6$): δ−32.5 (s). MS (m/z): 334 $[M]^+$.

EXAMPLE 1c

Synthesis of Sodium 1-tertbutyl-3-(diphenylphosphino)phenoxide. THF (hereinafter "the Na derivative of Ligand 1")

THF (50 ml) was added to a mixture of (Compound 1) (4.11 g, 12.3 mmol) and NaH (1.08 g, 45 mmol). The resultant slurry was stirred at 60° C. for 12 h. After cooling to room temperature the solution was filtered and the excess NaH washed with THF (20 ml). The THF solution was reduced in volume to around 15 ml and heptane (60 ml) added giving white crystals that formed over 12 h at room temperature. The crystals were filtered, washed with pentane (2×20 ml) and dried under vacuum to give the Na derivative of Ligand 1 (3.58 g, 8.35 mmol, 68% yield). Anal. Calcd for $C_{26}H_{30}O_2PNa$: C, 72.88; H, 7.06. Found: C, 72.96; H, 6.97. $^1H$ NMR ($C_6D_6$): δ 7.52-7.44 (m, 5H, $PC_6H_5+C_6H_3$), 7.15-7.04 (m, 6H, $PC_6H_5$), 6.82-6.76 (m, 1H, $C_3H_3$), 6.63-6.57 (m, 1H, $C_6H_3$), 3.17-3.12 (m, 4H, $OCH_2CH_2$), 1.64 (s, 9H, $C(CH_3)_3$), 1.21-1.13 (m, 4H, $OCH_2CH_2$). $^{13}C\{^1H\}$ NMR ($C_6D_6$): δ 171.0 (d, $^2J(PC)$=17 Hz, Ar—C), 139.1 (d, $^3J(PC)$=6 Hz, Ar—C), 136.6 (Ar—C), 134.0 (d, $^2J(PC)$=18 Hz, Ar—C), 130.7 (Ar—C), 127.4 (d, $^1J(PC)$=24 Hz, Ar—C), 122.7 (d, $^2J(PC)$=17 Hz, Ar—C), 112.3 (Ar—C), 67.6 ($CH_2CH_2O$), 34.8 ($C(CH_3)$), 30.0 ($C(CH_3)$), 25.0 ($CH_2CH_2O$). $^{31}P\{^1H\}$ NMR ($C_6D_6$): δ−17.8 (s).

EXAMPLE 2

Synthesis of (Ligand 1)$_2$MCl$_2$ (M=Ti, Zr)—General Procedure

A solution of the Na derivative of Ligand 1 (2 equivalents) in THF was transferred to a solution MCl$_4$(THF)$_2$ (1 eq.) in THF and stirred at room temperature for 12 h. The solvent was removed and the residue extracted with dichloromethane (2×20 ml). Removing the solvent gave an orange precipitate that was washed with pentane (20 ml) and dried under vacuum to give the complex.

EXAMPLE 2a

Synthesis of (Ligand 1)$_2$TiCl$_2$, ("Complex 1A")

Reaction of the Na derivative of Ligand 1 (0.428 g, 1 mmol) and TiCl$_4$(THF)$_2$ (0.167 g, 0.5 mmol) gave the complex (Complex 1A) as an orange solid (0.357 g, 0.45 mmol, 91% yield). $^1H$ NMR ($C_6D_6$): δ 8.07-7.98 (br t, 2H, Ar—H), 7.65-7.62 (br t, 2H, Ar—H), 7.30-7.21 (m, 3H, Ar—H), 7.03-6.65 (m, 19H, Ar—H), 1.67 (s, 9H, $C(CH_3)_3$), 1.26 (s, 9H, $C(CH_3)_3$). $^{31}P\{^1H\}$ NMR ($C_6D_6$): δ 11.9 (s), 9.5 (s).

EXAMPLE 2b

Synthesis of (Ligand 1)$_2$ZrCl$_2$; ("Complex 1B")

Reaction of the Na derivative of Ligand 1 (2.142 g, 5.0 mmol) and ZrCl$_4$(THF)$_2$ (0.943 g, 2.5 mmol) gave (Complex 1B) (1.816 g, 2.2 mmol, 88% yield). $^1H$ NMR ($C_6D_6$): δ 7.32-7.25 (br+m, 8H, Ar—H), 7.00-6.66 (m, 16H, Ar—H), 1.46 (s, 18H, $C(CH_3)_3$). $^{31}P\{^1H\}$ NMR ($C_6D_6$): δ−1.6 (s).

EXAMPLE 3

Ethylene polymerization using Complexes 1A and 1B—General Procedure

Polymerisations were performed by adding 5 μM of the Complex (pre-catalyst) (in 5 ml toluene solution) to 100 ml toluene containing 500 eq MAO under 2 bar ethylene pressure at 25° C. Polymerisations were run for 30 min and terminated by addition of 10% HCl/MeOH. Insoluble polymer was isolated by addition of 300 ml MeOH, filtration and washing with MeOH.

EXAMPLE 3a

Ethylene polymerisation with Complex 1A. Following the above procedure yielded 2.0 g of polyethylene, corresponding to an activity of 390 gmmol$^{-1}$ h$^{-1}$ bar$^{-1}$.

EXAMPLE 3b

Ethylene polymerisation with Complex 1B. Following the above procedure yielded 7.3 g of polyethylene, corresponding to an activity of 1460 gmmol$^{-1}$ h$^{-1}$ bar$^{-1}$.

EXAMPLE 4

Propylene polymerisation with Complex 1B

The polymerisation was started by addition of Complex 1B (2.5 μM in 10 ml toluene) to 100 ml heptane containing MAO (1000 eq) and TIBAL (25 eq) under 2 bar propylene pressure at 0° C. The polymerisations were run for 30 min and terminated by addition of 2M HCl (50 ml). The layers were separated and the organic fraction further washed with 2M HCl (2×30 ml), water (30 ml), dried (MgSO$_4$), filtered and the solvent removed to yield polypropylene that was dried under vacuum for 12 h. The yield of polymer was 5.3 g corresponding to an activity of 2125 gmmol$^{-1}$ h$^{-1}$ bar$^{-1}$.

Notes on the Examples:
Ac=Acetate
MAO=Methyl aluminoxane
TIBAL=Tri isobutylaluminium

EXAMPLE 5

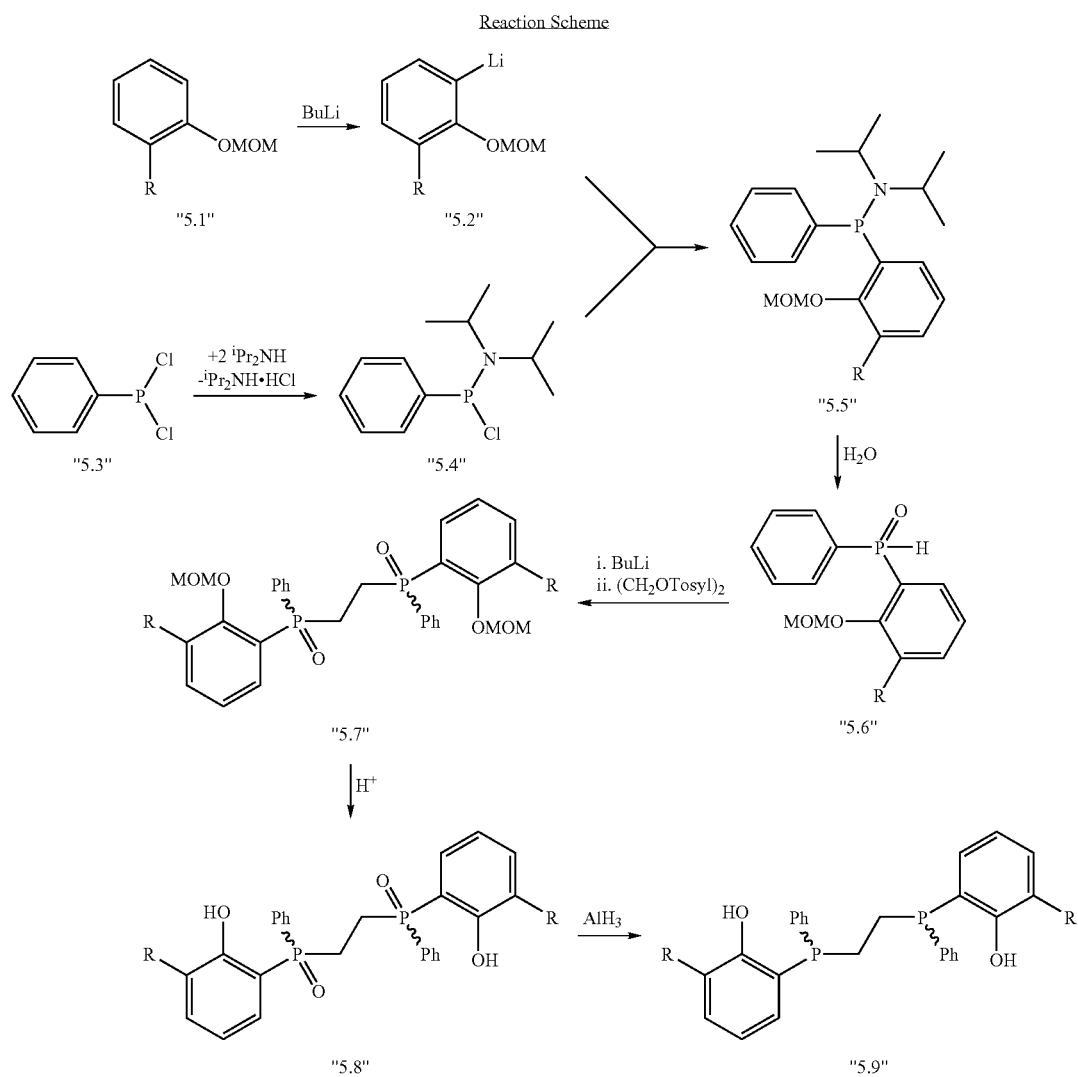

Reaction Scheme

Synthesis of 1-tert-butyl-2-methoxymethoxybenzene (Compound "5.1"):

See Note #1

The following reaction was carried out in an efficient fume cupboard. To a solution of 2-tert-butylphenol (322 g, 2.1 moles) dissolved in 1.5 liters of degassed HPLC grade thf (tetrahydrofuran) in a flask fitted with an efficient condenser was added chunks of sodium (52 g, excess) and the reaction mix allowed to react for 3 hours then refluxed overnight to complete the reaction. A solution of MOMCl was formed in a 3 liter, 3 neck flask fitted with an efficient double surfaced condenser, pressure equalizing dropping funnel and a nitrogen inlet in a water bath at RT by the slow addition of AcCl (205 g, 2.6 moles) to dimethoxymethane (229 g, 3.0 moles) with a catalytic amount of $ZnCl_2$ (2 g). Caution MOMCl is a known carcinogen and the reaction is exothermic!! After addition of the AcCl the reaction mixture is stirred for 30 minutes and the dropping funnel replaced with a septum. The thf solution of sodium phenolate added by cannula and the reaction mix stirred for 1 hour to complete the reaction. The reaction mix is deactivated by the addition of 500 mls of 2 M NaOH solution and stirring for a further 60 minutes to decompose excess MOMCl. Ether (500 mls) is added and the phases separated. The organic phase was washed with 3×500 mls of distilled water and dried over $MgSO_4$, filtered and the ether removed on a Rota-Vap. The unreacted phenol was removed by passage through a basic alumina column using hexane as elutriation solvent. The recovered material (compound "5.1") was purified by flash distillation under reduced pressure, 67-68° C. 0.4 mm Hg. Yield 287 g (74%). $^1$H-NMR (250 MHz, $CDCl_3$) δ 1.420(s, 9H, $C(CH_3)_3$), 3.519(s, 3H, OMe), 5.253 (s, 2H, $OCH_2O$), 6.92-7.33(m, 4H, Ar—H).

Synthesis of (3-tert-Butyl-2-methoxymethoxyphenyl)phenylphosphineoxide ("compound 5.6"):

Reaction completed under $N_2$.

To a solution of $PhPCl_2$ (14.0 g, 78.2 mmole) in 200 mls of dry toluene was added $iPr_2NH$ (15.82 g, 21.9 mls, 156 mmole) and the slurry stirred overnight. The precipitated $iPr_2NH.HCl$ was removed by filtration leaving a solution of "compound 5.4" in toluene. A slurry of "compound 5.2" was formed by addition of BuLi (31.3 mls, 2.5 M, 78.2 mmole) to a solution of "compound 5.1" (15.2 g, 78.2 mmole) in 100 mls of ether and stirring at RT overnight. The slurry of compound 5.2 was added to the toluene solution of "compound 5.4" cooled to −78° C. and the solution allowed to warm to RT (room temperature) and stirred for 1 hour to generate "compound 5.5" in situ. The reaction was deactivated by addition of 100 mls of distilled $H_2O$ and 100 mls of 2 M HCl and stirring for 4 hours. The organic phase was separated, washed with 2×100 mls of distilled water and dried over $Na_2SO_4$. The solvent was removed on a Roto-Vap. The crude product was purified by flash column chromatography with ether as elutriation solvent ($R_f$ 0.29 ether). Yield of a pale yellow oil 19.3 g (77.5%). $^{31}P\{^1H\}$-NMR (101 MHz, $CDCl_3$) δ 17.91 ppm.

Preparation of 1,2-Ethanediylbis{(3-tert-Butyl-2-methoxymethoxyphenyl)phenylphosphine oxide} ("Compound 5.7") see Note #2 below: Reaction completed under $N_2$.

To a solution of "compound 5.6" (10.0 g, 31.42 mmole) in 50 mls of THF at −20° C. (ice/acetone) was added slowly BuLi (12.25 ml, 2.5 M, 30.63 mmole) and the orange solution warmed to RT, reacted for 1 hour then cooled to −20° C. Ethylene glycol di-p-tosylate (5.56 g, 15.0 mmole) was added in lots over 15 minutes then the slurry warmed to RT, stirred for 1 hour then refluxed for 2 hours. The reaction mix was cooled to room temperature and deactivated by addition of distilled $H_2O$. The product was extracted with DCM (dichloromethane) and the combined DCM extracts were washed with 3×50 mls of $H_2O$ and dried over $Na_2SO_4$. The DCM was removed under vacuum and the residue triturated with hexane overnight. The crude product was recovered by filtration. FW 662.75. Yield 45%. $^{31}P\{^1H\}$-NMR (101 MHz, $CDCl_3$) 35.41 and 35.69 ppm. Crystals suitable for structural determination were isolated from a benzene solution of "Compound 5.7" layered with hexane indicating the presence of a RS/SR diasteriomeric pair. $^{31}P\{^1H\}$-NMR (101 MHz, $CDCl_3$) δ 35.69 ppm.

Preparation of 1,2-Ethanediylbis{(3-tert-Butyl-2-hydroxyphenyl)phenylphosphine oxide} ("compound 5.8"):

A sample of "Compound 5.7" (6 g, 9.05 mmole) was dissolved in 50 mls of HOAc and 5 mls of $H_2O$ added. The reaction mix was heated to reflux for 2 hours, cooled and the product extracted with EtOAc, the extracts washed with 50 mls $H_2O$ dilute $NH_3$ then $H_2O$. The EtOAc layer was dried over $Na_2SO_4$, filtered and the solvent removed under vacuum. The residue was extracted with MeOH at RT to leave an insoluble material and a second fraction was recovered by cooling the MeOH solution to −78° C. A separate deprotection of "compound 5.7" (RS/SR) isolated from above lead to the MeOH insoluble product. FW 574.64. Yield (MeOH sol. RR/SS) 1.5 g (28.8%), $^{31}P\{^1H\}$-NMR (101 MHz, $CDCl_3$) δ 46.70 ppm. Yield (MeOH insol. RS/SR) 2.2 g (42.3%), $^{31}P\{^1H\}$-NMR (101 MHz, $CDCl_3$) δ 46.79 ppm.

Preparation of 1,2-Ethanediylbis{(3-tert-Butyl-2-hydroxyphenyl)phenylphosphine} ("Compound 5.9"): Reaction completed under $N_2$.

To a solution of "Compound 5.8"(RR/SS) (0.72 g, 1.25 mmole) in 5 ml of thf was added $AlH_3$ [formed by the slow addition of conc. $H_2SO_4$ (0.613 g, 0.33 ml, 6.25 mmole) to a slurry of $LiAlH_4$ (0.474 g, 12.5 mmole) in 50 mls of thf, stirred overnight, allowed to settle and filtered] and the reaction mix heated to reflux for 2 hours, cooled and deactivated by the slow addition of HOAc, then $H_2O$. The product was recovered by extraction into ether. The ether layer was washed with 3×50 mls of $H_2O$ and dried over $Na_2SO_4$, filtered and dried under vacuum. Racemisation was observed. $^{31}P\{^1H\}$-NMR (101 MHz, $CDCl_3$) δ−43.26 and δ−43.33 ppm. FW 542.64. The products were isolated by extraction with MeOH to give MeOH insol. RS/SR, yield 0.28 g (41%) $^3P\{^1H\}$-NMR (101 MHz, $CDCl_3$) δ−43.33 ppm, and MeOH sol. RR/SS, yield 0.21 g (30.9%) $^{31}P\{^1H\}$-NMR (101 MHz, $CDCl_3$) δ−43.25 ppm. Assignments were made by partial reduction of "Compound 5.8" (RS/SR) to give mainly product at $^{31}P\{^1H\}$-NMR δ−43.33 while partial reduction of "compound 5.8" (RR/SS) gave mainly product at $^{31}P\{^1H\}$-NMR δ−3.25.

Notes

1 Method of Hibbert, F. Spiers, K. J., Journal of the Chemical Society-Perkin Transactions 2, 1989, 377-380.

2 Modified Method of Wife, R. L.; Vanoort, A. B.; Vandoorn, J. A. Vanleeuwen, P., Synthesis, 1983, 71-73.

EXAMPLE 6

Polymerisation of α-olefins using "[OPPO]VO(OPr)" ie the ligand "compound 5.9" prepared in Example 5

Ethylene Polymerisation. A Fischer-Porter Reactor was filled with dry heptane (200 ml) under a nitrogen atmosphere. The reactor was placed under 2 bar ethylene pressure at room temperature and DMAC (1M in hexane) was added. Where used, ethyl trichloroacetate was also added. The catalyst was prepared by addition of a toluene solution of $VO(O_nPr)_3$ to a toluene solution of ligand "compound 5.9" (prepared in Example 5) (in a 1:1 molar ratio) and activated by addition of DMAC (30 eq.) followed by stirring for 2 min. After stirring the reactor mixture for 5 min, the catalyst was injected. The polymerisation was terminated by addition of 2M HCl and MeOH and the polymer collected by filtration, washed with MeOH and dried at 60° C. under vacuum. DMAC is dimethyl aluminium chloride.

| Run 1. | Catalyst loading = 5.0 μmol |
| --- | --- |
| | DMAC = 0.85 mmol |
| | Ethyl trichloroacetate = 0.0 mmol |
| | Run Time = 1 h |
| | Exotherm = 2.5° C. |
| | Polymer yield = 1.93 g |
| | Activity = 193 g/mmol · h · bar |
| Run 2. | Catalyst loading = 5.0 μmol |
| | DMAC = 0.85 mmol |
| | Ethyl trichloroacetate = 1.0 mmol |
| | Run Time = 15 min |
| | Exotherm = 43° C. |
| | Polymer yield = 10.23 g |
| | Activity = 4092 g/mmol · h · bar |
| Run 3. | Catalyst loading = 0.5 μmol |
| | DMAC = 0.99 mmol |
| | Ethyl trichloroacetate = 1.0 mmol |
| | Run Time = 1 h |
| | Exotherm = 3.2° C. |
| | Polymer yield = 0.72 g |
| | Activity = 720 g/mmol · h · bar |

The invention claimed is:

1. A transition metal complex having the following Formula A:

$$\left( \begin{array}{c} R^2 \\ R^3 \end{array} \begin{array}{c} R^1 \\ E \\ O \end{array} M(X)_y(L)_z \right)_n$$

Formula A wherein the monovalent groups $R^1$ and $R^2$ are independently selected from $-R^a$, $-OR^b$, $-NR^cR^d$, and $-NHR^e$;

the monovalent groups $R^a$, $R^b$, $R^c$, $R^d$, and $R^e$, and the divalent group $R^3$ are independently selected from (i) aliphatic hydrocarbon, (ii) alicyclic hydrocarbon, (iii) aromatic hydrocarbon, (iv) alkyl substituted aromatic hydrocarbon (v) heterocyclic groups and (vi) hetero-substituted derivatives of said groups (i) to (v);

M is vanadium; E is phosphorus or arsenic; X is an anionic group, L is a neutral donor group; n is 1 or 2, y and z are independently zero or integers such that the number of X and L groups satisfy the valency and oxidation state of the metal M.

2. A transition metal complex as claimed in claim 1 wherein E is phosphorus.

3. A transition metal complex as claimed in claim 1 wherein the anionic group X is selected from halide, a hydrocarbyl group, a carboxylate, an oxide, an amide, an alkoxide; an acetylacetonate, a hydroxyl and a non-coordinating or weakly-coordinating anion selected from tetrafluoroborate, a fluorinated aryl borate and a triflate.

4. A transition metal complex as claimed in claim 1 wherein the anionic groups X are monoanionic, dianionic or trianionic.

5. A transition metal complex as claimed in claim 1 wherein the neutral donor group L is selected from a solvate molecule, an amine, a phosphine, an olefin, water or a conjugated or nonconjugated diene.

6. A catalyst system for the polymerisation of unsaturated monomer comprising
   (1) a complex compound having the Formula A as claimed in claim 1 and
   (2) an activator compound.

7. A catalyst system as claimed in claim 6 wherein the activator compound is selected from organoaluminium compounds and organoboron compounds.

8. A catalyst system as claimed in claim 7 wherein the activator compound is selected from trimethylaluminium, triethylaluminium, tributylaluminium, tri-n-octylaluminium, ethylaluminium dichloride, diethylaluminium chloride, methylaluminium dichloride, dimethylaluminium chloride, tris(pentafluorophenyl) aluminium, alumoxanes, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)$[(bis-3,5-trifluoromethyl)phenyl]borate, trityltetra(pentafluorophenyl)borate and tris(pentafluorophenyl) boron.

9. A polymerisation catalyst system as claimed in claim 6 wherein the activator is provided by a Lewis acid selected from
   (a) ionic-bonding compounds having a $CdCl_2$ type or a $CdI_2$ type of layered crystal structure;
   (b) clays, clay minerals, or ion-exchange layered compounds;
   (c) heteropoly-compounds; and
   (d) halogenated lanthanoid compounds.

10. A polymerisation catalyst system as claimed in claim 6 wherein there is present a promoter comprising a halogenated organic compound.

11. A polymerisation catalyst system as claimed in claim 10 wherein the promoter is selected from carbon tetrachloride, hexachloroethylene, benzylbromide, benzylchloride, ethyl trichloroacetate and 2,3- or 1,3-dichloropropylene, chloroform ($CHCl_3$) and n-butylchloride.

12. A polymerisation catalyst system as claimed in claim 6 wherein the catalyst is on a support material selected from silica, alumina, zirconia, magnesia, magnesium chloride, a polymer or prepolymer.

13. A polymerisation catalyst as claimed in claim 6 wherein in addition to the defined catalyst there is present one or more other catalysts for polymerising 1-olefins.

14. A polymerisation catalyst as claimed in claim 6 wherein in addition to the defined catalyst there is present one or more other transition metal catalysts selected from Ziegler-Natta catalyst systems, metallocene-based catalysts and heat activated supported chromium oxide catalysts.

15. A process for the polymerisation and copolymerisation of 1-olefins, cycloolefins or dienes comprising contacting the monomeric olefin under polymerisation conditions with the polymerisation catalyst system claimed in claim 6.

16. A process as claimed in claim 15 wherein the process is for the homopolymerisation of 1-olefins and wherein the monomer is selected from ethylene, propylene, butene, hexene, and styrene.

17. A process as claimed in claim 15 wherein the process is for the copolymerisation of 1-olefins and wherein the monomer is selected from ethylene, propylene, 1-butene, 1-hexene, 4-methylpentene-1, 1-octene, methyl methacrylate, methyl acrylate, butyl acrylate, acrylonitrile, vinyl acetate, vinyl chloride, styrene, butadiene, hexadiene and norbornene.

18. A process as claimed in claim 15 comprising the copolymerisation of ethylene and or propylene with comonomers selected from 1-butene, 1-hexene, 4-methylpentene-1, methyl methacrylate, methyl acrylate, butyl acrylate, acrylonitrile, vinyl acetate, and styrene, diene, cyclic olefin, norbornene and substituted norbornene.

19. A process as claimed in claim 15 wherein the process is carried out under gas phase, slurry phase or solution phase polymerisation conditions.

20. A process as claimed in claim 15 wherein the process is carried in the presence of hydrogen gas to modify the average molecular weight of the produced polymer.

* * * * *